(12) United States Patent
Lasry et al.

(10) Patent No.: US 12,369,801 B2
(45) Date of Patent: Jul. 29, 2025

(54) SENSING MICROSYSTEM AND RELATED METHOD OF MANUFACTURING

(71) Applicant: iMD Research Inc., Montréal (CA)

(72) Inventors: Nathaniel Lasry, Montreal (CA); Mervyn Gornitsky, Westmount (CA); Hyman Morris Schipper, Cote-Saint-Luc (CA); Sharmistha Bhadra, Montreal (CA); Seyedfakhreddin Nabavi, Montreal (CA)

(73) Assignee: iMD Research Inc., Montreal (CA)

( * ) Notice: Subject to any disclaimer, the term of this patent is extended or adjusted under 35 U.S.C. 154(b) by 399 days.

(21) Appl. No.: 17/692,847

(22) Filed: Mar. 11, 2022

(65) Prior Publication Data

US 2022/0287573 A1    Sep. 15, 2022

Related U.S. Application Data

(60) Provisional application No. 63/159,820, filed on Mar. 11, 2021.

(51) Int. Cl.
*A61B 5/02* (2006.01)
*A61B 5/00* (2006.01)
*A61B 5/0205* (2006.01)

(52) U.S. Cl.
CPC .......... *A61B 5/0205* (2013.01); *A61B 5/0022* (2013.01); *A61B 5/0024* (2013.01)

(58) Field of Classification Search
None
See application file for complete search history.

(56) References Cited

U.S. PATENT DOCUMENTS

| | | | |
|---|---|---|---|
| 2014/0012102 A1* | 1/2014 | Das | A61B 5/6801 600/595 |
| 2015/0263673 A1* | 9/2015 | Biel | A61B 5/25 600/372 |
| 2020/0069226 A1* | 3/2020 | Hahn | A61B 5/053 |

* cited by examiner

*Primary Examiner* — Sana Sahand
(74) *Attorney, Agent, or Firm* — Benoit Yelle; Lavery De Billy LLP

(57) ABSTRACT

A sensing microsystem that can be used to sense various physiological parameters of a subject is disclosed. The sensing microsystem comprises one or more sensors for collecting data that can be used to accurately determine various vital sign and/or other physiological parameters of the subject, and further comprises a communication module that allows the microsystem to communicate remotely with an external device via one or more communications protocols. The one or more sensors and the communication module are disposed on respective electronics-compatible substrates that are electrically coupled with a power source. An isolated communication channel that communicatively couples the one or more sensors and the communication interface is at least partially defined by and extends through the power source.

10 Claims, 5 Drawing Sheets

SENSING MICROSYSTEM AND RELATED METHOD OF MANUFACTURING

CROSS-REFERENCE TO RELATED APPLICATIONS

This application claims benefit of U.S. provisional application No. 63/159,820, filed Mar. 11, 2021, which is herein incorporated by reference in its entirety.

TECHNICAL FIELD

The present invention relates to sensing technologies, and in particular to miniaturized sensing systems.

BACKGROUND

The demand for devices that measure/monitor physiological parameters of human subjects is ever increasing. Continuous monitoring of physiological parameters, such as body temperature (T), heartrate (HR), blood pressure (BP), blood oxygen saturation (SpO2), and respiratory rate (RR), is routinely performed in hospitals with non-wearable bulky monitoring units. Smaller, wearable systems have been designed to monitor physiological parameters of patients as well as generally healthy people who are interested in monitoring such physiological parameters (such as athletes, etc.). However, there is continued demand to make physiological-sensing devices smaller. Attempting to miniaturize physiological-sensing devices encounters several problems, such as how to make the device smaller without comprising battery life or wireless communication capabilities. Additionally, noise poses a significant challenge as electrical components are brought closer together.

The present invention addresses the need for miniaturized sensing systems.

SUMMARY

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One general aspect includes a sensing microsystem, comprising a power source, a first electronics-compatible substrate electrically coupled with the power source, the first electronics-compatible substrate having one or more sensors disposed thereon and a second electronics-compatible substrate electrically coupled with the power source, the second electronics-compatible substrate having a communication module disposed thereon, wherein the power source at least partially defines an isolated communication channel extending therethrough, and wherein the communication module and the one or more sensors are communicatively coupled via the at least one isolated communication channel.

In implementations of the sensing microsystem, the first electronics-compatible substrate is arranged at a first surface of the power source, the second electronics-compatible substrate is arranged at a second surface of the power source opposite the first surface, and the isolated communication channel extends between the first surface and the second surface of the power source.

In implementations of the sensing microsystem, the one or more sensors are coupled with a first transceiver disposed at a first end of the isolated communication channel, and wherein the communication module is coupled with a second transceiver disposed at a second end of the isolated communication channel.

In implementations of the sensing microsystem, in the isolated communication channel is an optical communication channel that is optically isolated.

In implementations of the sensing microsystem, the isolated communication channel is an electrical communication channel that is electrically isolated.

In implementations of the sensing microsystem, the electrical communication channel is further isolated from magnetic interference.

In implementations of the sensing microsystem, the communication module is configured to wirelessly communicate with an external device.

Implementations of the sensing microsystem may include a processing module communicatively coupled with the one or more sensors and the communication module, and wherein the processing module is configured to receive data from the one or more sensors, perform processing on the data, and send the processed data to the communication module.

Implementations of the sensing microsystem may include a memory to store data from the one or more sensors, and/or the processed data.

In implementations of the sensing microsystem, the one or more sensors comprise sensors for measuring a physiological parameter of a subject.

In implementations of the sensing microsystem, the one or more sensors comprise a GPS module.

In implementations of the sensing microsystem, the sensing microsystem has a surface area of length by width of less than 1 cm$^2$.

In implementations of the sensing microsystem, the sensing microsystem has a thickness of less than 7 mm.

Another general aspect includes a method of manufacturing a sensing microsystem, comprising: arranging one or more sensors on a first electronics-compatible substrate; arranging a communication module on a second electronics-compatible substrate; defining an isolated communication channel through a power source; and arranging the first and second electronics-compatible substrates with respect to the isolated communication channel.

In implementations of the method, the first electronics-compatible substrate is arranged at a first surface of the power source, the second electronics-compatible substrate is arranged at a second surface of the power source opposite the first surface, and the isolated communication channel extends between the first surface and the second surface of the power source.

In implementations of the method, the one or more sensors are coupled with a first transceiver, the communication module is coupled with a second transceiver, and wherein arranging the first and second electronics-compatible substrates with respect to the isolated communication channel comprises arranging the first transceiver at a first end of the isolated communication channel and arranging the second transceiver at a second end of the isolated communication channel.

In implementations of the method, defining the isolated communication channel through the power source comprises optically isolating the communication channel.

In implementations of the method, defining the isolated communication channel through the power source comprises electrically isolating the communication channel.

BRIEF DESCRIPTION OF THE DRAWINGS

Further features and exemplary advantages of the present invention will become apparent from the following detailed description, taken in conjunction with the appended drawings, in which.

DETAILED DESCRIPTION

Figure 1:
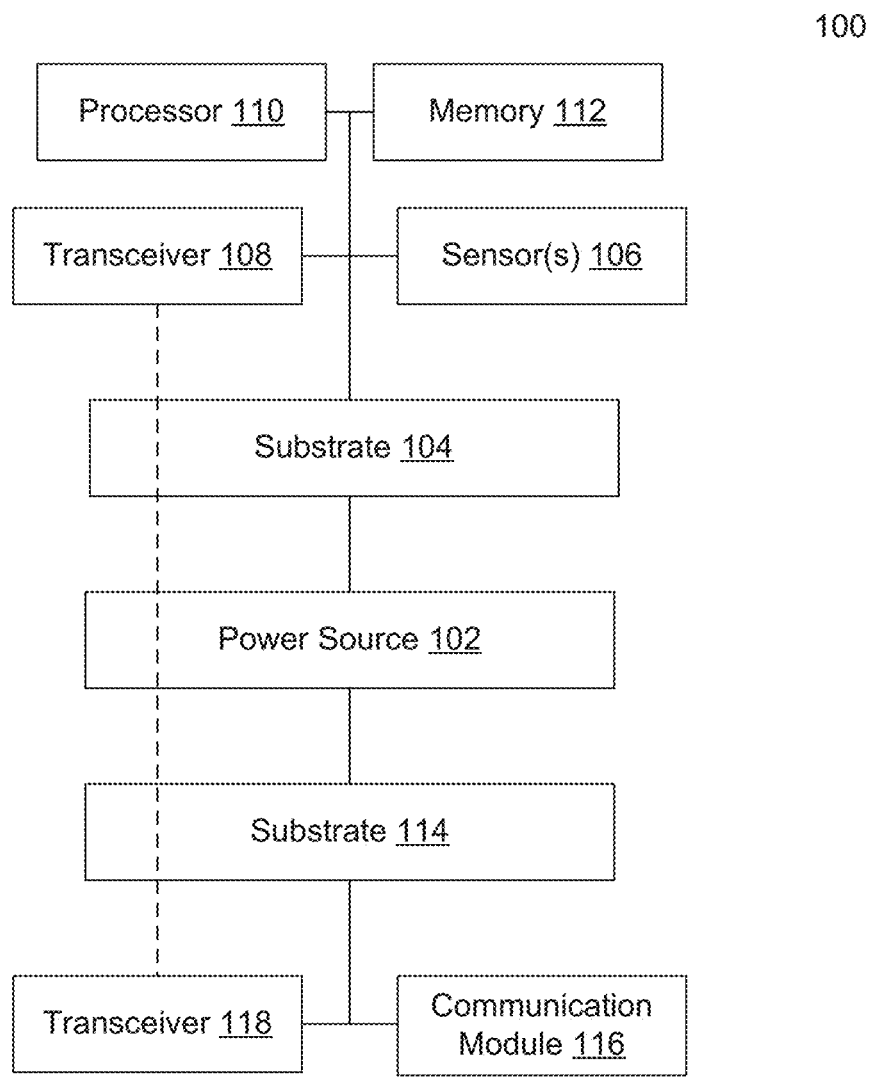
FIG. 1 is a schematic diagram showing a configuration of a sensing microsystem 100 in accordance with the teachings of the present invention.

The present disclosure describes a sensing microsystem that can be used to sense various physiological parameters of a subject, including but not limited to temperature (T), heart rate (HR), blood pressure (BP), oxygen saturation (SPO2) and respiratory rate (RR), biopotential and bioimpedance. The sensing microsystem comprises one or more sensors for collecting data that can be used to accurately determine various vital sign and/or other physiological parameters of the subject, and further comprises a communication module that allows the microsystem to communicate remotely with an external device via one or more communications protocols. The sensing microsystem thus allows for continuous, real-time monitoring of the physiological-parameters of the subject, and is able to communicate wirelessly with one or more external devices for remote monitoring. A GPS module may also be provided for determining a location of the sensing microsystem. The sensing microsystem further comprises a power source such as a rechargeable battery, and is designed to have very low power consumption, within a few hundreds of microwatts, in order to extend the battery life. The sensing microsystem may be very small (less than 1 cm$^2$ and with a thickness of less than 7 mm), and may therefore be readily incorporated into various devices such as wearable devices, intra-oral devices, etc., and may in some applications even be implanted into a subject.

The one or more sensors and the communication module are disposed on respective electronics-compatible substrates that are electrically coupled with the power source. At these very small sizes with dimensions on the order of less than 1 cm, noise caused by electrical interference is a particular challenge that can lower signal to noise ratios and plague data. In the sensing microsystem disclosed herein, an isolated communication channel that communicatively couples the one or more sensors and the communication interface is at least partially defined by and extends through the power source. This advantageously helps to reduce noise between data acquisition at the one or more sensors and communications processing at the communications interface. The isolated communication channel may be an optical communication channel or an electrical communication channel. In an exemplary configuration, the one or more sensors are disposed on a first electronics-compatible substrate arranged at a first surface of the power source, and the communication module is disposed on a second electronics-compatible substrate arranged at a second surface of the power source that is opposite to the first surface. In this configuration, the isolated communication channel extends between the first and second surfaces of the power source.

To appreciate the present contributions to the art, the above descriptions of the more important features of the invention are provided broadly to better understand the detailed descriptions that follow. Together with the accompanying figures and following descriptions, other aspects and features of the invention will become apparent. The drawings are solely provided for the purposes of illustration. In no way do they constitute a definition of the limits of the invention as defined in the claims below. Embodiments will be described below, by way of example only, with reference to FIGS. 1-5.

FIG. 1 is a schematic diagram showing a configuration of a sensing microsystem in accordance with the teachings of the present invention. The solid lines connecting components shown in FIG. 1 represent an electrical coupling. The dashed line shown in FIG. 1 represents a communication channel. As described in further detail below, the communication channel may be an optical communication channel that is optically isolated, or an electrical communication channel that is electrically isolated. In the description below, when two components are described as being coupled, these components may be connected with one another directly or indirectly, i.e. through one or more other components.

The microsystem comprises a power source 102 that provides electrical power to the microsystem. The power source 102 may for example comprise a rechargeable battery, such as a LiPo battery or any other type of rechargeable battery, but it may also be a single charge battery. The microsystem is designed to have very low power consumption requirements, and as such the energy capacity of the power source 102 may be quite low, such as 12 mAh. Accordingly, the power source 102 may be quite small, and may for example have a surface area of length by width no greater than 1 cm$^2$. In some embodiments, the microsystem may have an interface that allows the power source to be charged via a charging port. In some embodiments, the power source may be rechargeable (wirelessly rechargeable batteries; gyroscope-based rechargeable batteries; solar-power rechargeable batteries).

The power source 102 is electrically coupled to a first electronics-compatible substrate 104 and a second electronics-compatible substrate 114. In some embodiments, the power source 102 may be electrically coupled to the first electronics-compatible substrate 104 and the second electronics-compatible substrate 114 via a wired connection. In some embodiments, the power source 102 is electrically coupled to the first electronics-compatible substrate 104 and the second electronics-compatible substrate 114 via contacts and/or wirelessly. In a preferred arrangement, the first electronics-compatible substrate 104 and the second electronics-compatible substrate 114 are separated by the power source 102 there-between. That is, the first electronics-compatible substrate 104 is arranged at a first surface of the power source 102, and the second electronics-compatible substrate 114 is arranged at a second surface of the power source 102 opposite to the first surface.

Each of the first and second electronics-compatible substrates 104, 114, may comprise a semiconductor material with an interposer. In some embodiments, the first and second electronics-compatible substrates 104, 114 may be flexible to conform to various geometries.

One or more sensors 106 are arranged on the first electronics-compatible substrate 104. The sensor(s) 106 are sensors that collect data indicative of one or more physiological parameters of a subject. Different sensors may be used depending on the application and the specific physiological parameters of interest in monitoring. As further described herein, the microsystem may be incorporated into a wearable device to be worn by a subject and/or inserted into a cavity (e.g. oral cavity) of the subject, or may be implanted in the subject. As further described herein and as would be appreciated by a person skilled in the art, the sensor(s) 106 are appropriately arranged at different locations on the first electronics-compatible substrate to accurately collect the data of interest. For example, some sensors may be arranged to be in contact or close proximity with one or more blood vessels of the subject. When incorporated into a wearable device, one or more openings may be provided where one or more of the different measurement devices may be positioned in direct contact with the wearer is required.

The sensor(s) 106 may comprise a Photoplethysmography (PPG) sensor. PPG sensors are non-invasive low-cost sensors that monitor cardiorespiratory parameters. PPGs are comprised of one or more light sources, at one or more distinct wavelengths, and a photodiode. Each light source transmits at a given wavelength and the photodiode measures the reflected/transmitted lights from/through the skin. As blood flow changes with each heartbeat, a photodetector then records the variation of optical intensity. The PPG signals may be used to accurately measure vital signs such as HR, BP, SpO2, and RR. For example, data produced by a plurality of photoplethysmogram (PPG) sensors and a Pulse Transit Time (PTT) may be combined to compute the blood pressure in real time. Hence, using a set of well-defined algorithms, a single PPG sensor can be used to cost-efficiently measure four key vital signs.

The sensor(s) 106 may comprise an inertial module which may comprise an accelerometer and/or gyroscope and/or magnetometer sensor. The one or more accelerometer and/or gyroscope sensors can be used to measure movements and body vibrations of the subject. The accelerometer and/or gyroscope sensors may also be particularly useful to remove motion artifacts that reduce the accuracy of measurements with PPG sensors as well as for actigraphy. The magnetometer can be used to determine accurately the position of the object in space: Pitch, Yaw and Roll. The magnetometer may be particularly useful for determining if a person lying down is lying face up, sideways, etc.

The sensor(s) 106 may comprise a pressure transducer or a pressure switch. The pressure transducer or the pressure switch can be used to measure variations in air pressure. For example, when used intra-orally the pressure transducer or pressure switch may be used to indicate respiratory frequency and/or occlusal pressure, which could be useful to monitor bruxism.

The sensor(s) 106 may comprise a temperature sensor. The temperature sensor can be used to measure variations in a subject's temperature.

The sensor(s) 106 may comprise EEG (Electroencephalography) probes. The EEG probes can be used to measure electroencephalography data.

The sensor(s) 106 may comprise electrocardiogram (EKG or ECG) probes. The ECG probes can be used to measure heart performance data. The ECG probes may, for instance, take the form of small microelectromechanical systems (MEMS).

The sensor(s) 106 may comprise biopotential and/or bioimpedance sensors.

Bioimpedance can be used to triangulate blood pressure, and it can also be used to measure skin conductance and arousal. Biopotential can be used to extract EEG, ECG, or EMG. A biopotential sensor could also be used in addition to these other sensors such as an ECG sensor in parallel, and used for training an AI algorithm to convert the biopotential signal into an ECG signal. Using AI algorithms, combining the biopotential ECG information to the PPG heart rate signal can provide more accurate blood pressure readings.

The sensor(s) 106 may comprise a sound sensor. The sound sensor can be used to measure variations in sound (e.g., breathing effort).

The sensor(s) 106 may comprise a blood-chemical sensor. The blood-chemical sensor can be used to measure variations in blood levels of one or more chemicals present in the wearer's blood. Examples of blood chemical that may be measured include cortisol and glucose.

The sensor(s) 106 may further comprise a GPS module or a cellular connection chip, to locate the sensing microsystem. The GPS module can be useful for determining a location of a subject. As one example use case, a sensing microsystem that comprises a GPS module used by a person with dementia can be used for locating them should they get lost.

As shown in FIG. 1, the one or more sensors 106 are coupled to a first transceiver 108. The first transceiver may be arranged on the first electronics-compatible substrate 104. The first transceiver 108 is configured to receive sensor data and transmit data over the isolated communication channel. The first transceiver 108 may be an optical transceiver or an electrical transceiver depending on the type of communication channel. As represented in FIG. 1, and as will be described in more detail herein below, the isolated communication channel is at least partially defined by the power source 102.

The one or more sensors 106 may also be coupled to a processor 110 and a memory 112. The processor 110 may represent a single processor with one or more processor cores or an array of processors, each comprising one or more processor cores and a memory module, which may comprise various types of memory (different standardized or kinds of Random Access Memory (RAM) modules, memory cards, Read-Only Memory (ROM) modules, programmable ROM, etc.). In this configuration, the processor 110 may be used to process the data, which may be performed continuously and in real-time. The processor 110 may perform preliminary processing on the sensor data or may determine physiological parameters based on the sensor data. Preliminary processing of the data may involve performing a data cleaning of the data collected by the different sensors. For instance, the data cleaning may be used to remove noise that can be attributed to external sources or to remove other unwanted data. The memory 112 may be used to store the sensor data, preliminarily processed data, and/or determined physiological parameters. The processor 110 and the memory 112 may be coupled with the transceiver 108 to provide data thereto for transmission.

In the context of the described embodiments, runtime execution, real-time execution or real-time priority processing execution corresponds to operations executed while collecting the sensor data. An operation performed at runtime, in real-time or using real-time priority processing thus typically needs to meet certain performance constraints that may be expressed, for instance, in terms of maximum time and/or maximum number of processing cycles. Skilled persons will readily recognize that real-time processing may not actually be achievable in absolutely all circumstances.

As shown in FIG. 1, the second electronics-compatible substrate 114 comprises a communications module 116 disposed thereon. The communication module 116 is coupled with a second transceiver 118 that is configured to communicate with the first transceiver 108 via the isolated communication channel. The second transceiver 118 may be disposed on the second electronics-compatible substrate 114 at the other end of the isolated communication channel from the first transceiver 108. The communication module 116 can thus receive data collected by the sensors 106 and/or processed by the processor 110 for transmission to an external device. The communication module 116 may be configured to communicate with any appropriate short- or long-range wireless communication protocol, including but not limited to Bluetooth™, Zigbee™, Wi-Fi™, Ant+™ 4G, 5G, LTE, or Narrow Band IoT protocols such as LoRa, Sigfox and others, etc.

Advantageously, by separating the communication module 116 and the one or more sensors 106 by the power source 102, and by limiting communication between these components to an isolated communication channel that is at least partially defined by the power source 102, a reduction in noise can be achieved between the communication processing and signal acquisition despite the miniature size of the microsystem.

Figure 2A:
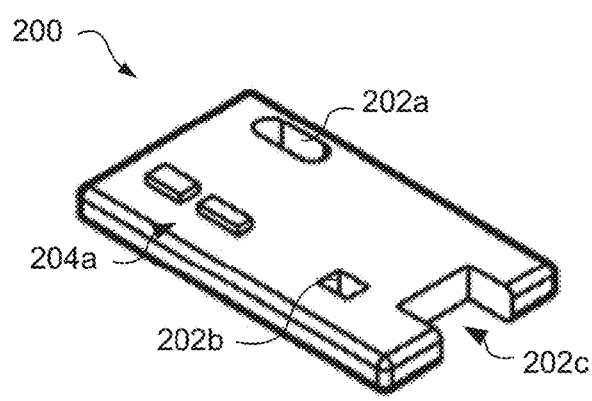
FIGS. 2A and 2B show an example power source used in the sensing microsystem in accordance with the teachings of the present invention.
Figure 2B:
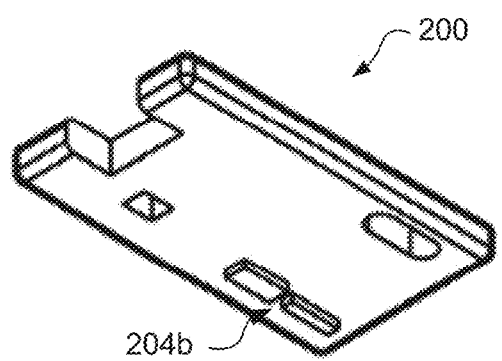

FIGS. 2A and 2B show an example power source 200 used in the sensing microsystem in accordance with the teachings of the present invention. Specifically, FIG. 2A shows an isometric top view and FIG. 2B shows an isometric bottom view of the power source 200. As described with reference to FIG. 1, the power source 200 may comprise a battery such as a rechargeable battery. Importantly, the power source 200 is designed to at least partially define at least one communication channel.

In the example power source 200 depicted in FIGS. 2A and 2B, the power source 200 comprises multiple holes extending there-through that may define respective communication channels. In FIGS. 2A and 2B, the power source 200 comprises three different holes 202a-c extending through a thickness of the power source and that may serve as communication channels.

The hole 202a is shown as an elliptical hole; the hole 202b is shown as a square or rectangular hole, and the hole 202c is shown as a cut-out or recess extending inward from a side surface of the battery. The holes 202a and 202b define an isolated communication channel that extends through the battery. The hole 202c partially defines an isolated communication channel extending there-through, and the communication channel may be isolated by wrapping the battery with an appropriate material (not shown). In these configurations, an isolated communication channel can be obtained that extends through the battery. The isolated communication channel may be an optical channel. In this case, there is no requirement for wiring such as optical fiber, as the communication can be transmitted through the air within the channel. The inner surfaces of the optical communication channel defined by the battery (and the wrapping material, if any) must be appropriately selected to transmit the optical signal and minimize any external interference. Suitable opaque materials should be used for defining an optical shield. Alternatively, the isolated communication channel may be an electrical channel. In this case, an electrically conductive medium such as a wire may be provided through the communication channel to couple the first and second transceivers. The electrical communication channel may be electrically isolated using electrical insulators. With electrical signals travelling between the transceivers, it may also be desirable to reduce electromagnetic noise by reducing magnetic interference as well. To reduce magnetic interference, materials such as a mu-metal or permalloy could be used.

As also previously described with reference to FIG. 1, the sensing microsystem comprises first and second electronics-compatible substrates that are electrically coupled to the power source. To avoid the use of additional electrical wiring, which could contribute to electrical interference and noise present within the microsystem, the power source 200 may be configured to provide electrical connection to the first and second electronics-compatible substrates via contact. For example, as shown in FIGS. 2A and 2B the power source 200 may comprise electrical contacts 204a and 204b on respective of its top and bottom surfaces that the first and second electronics-compatible substrates interface with. The electrical contacts 204a and 204b may be embossed as shown, or may be flat or depressed (not shown) from the outer surface of the power source. The first and second electronics-compatible substrates may be configured to interface with the electrical contacts 204a and 204b. Providing an electrical connection through the use of the electrical contacts 204a and 204b may also help to improve the overall structural stability of the microsystem.

While FIGS. 2A and 2B describe one example configuration of the power source, a person skilled in the art will appreciate that the power source is not limited to the design as shown in the drawings. For example, the power source 200 is shown as having a generally rectangular or pouch shape, while a power source of various other shapes such as cylindrical, etc., may be used. Further, while the power source 200 shows different shapes and sizes of holes 202a-c, other shapes and sizes of holes, as well as fewer or more holes, may be present. The holes may also extend in different directions through the power source, such as in a length or width direction, and the holes may also extend in more than one direction.

In another implementation, the power source may comprise a battery pack. For example, the power source may comprise a plurality of batteries such as that which is depicted in FIGS. 2A and 2B (or alternative configurations noted above), with holes in one or more of the batteries to define communication channels. In still another implementation, the battery pack could comprise several batteries with no holes in any of the batteries, but instead with a communication channel defined by the arrangement of the batteries themselves.

Figure 3A:
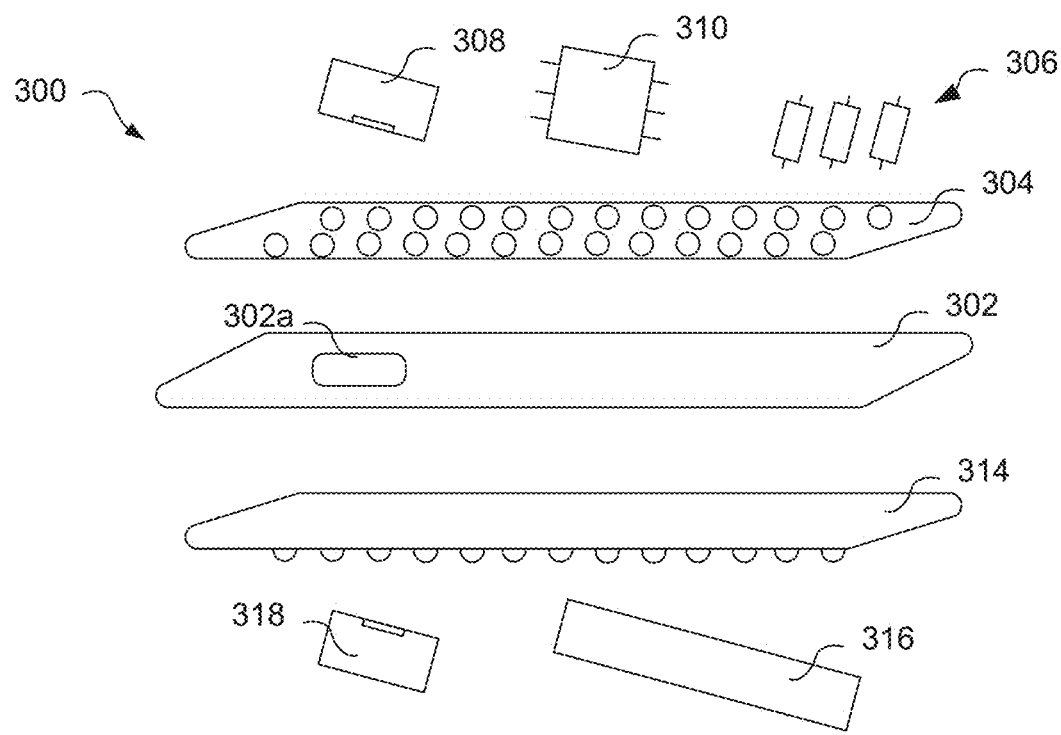
FIGS. 3A and 3B respectively show an exploded view and an assembled view of a representation of the sensing microsystem in accordance with the teachings of the present invention.
Figure 3B:
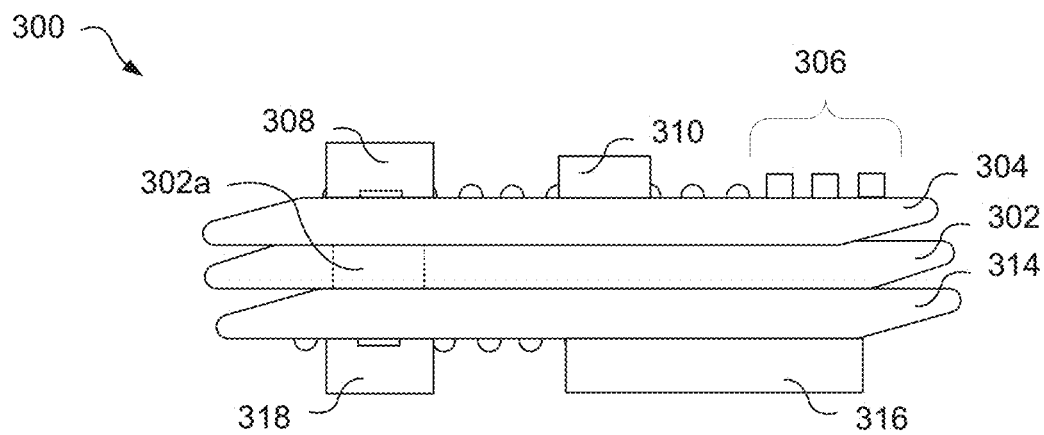

FIGS. 3A and 3B respectively show an exploded view and an assembled view of a representation of the sensing microsystem 300 in accordance with the teachings of the present invention. As previously described, the sensing microsystem 300 is miniature, with dimensions of length by width by height on the order of 1 cm by 1 cm by 0.7 cm or less.

The sensing microsystem 300 comprises a power source 302, a first electronics-compatible substrate 304 arranged at a first surface of the power source 302, and a second electronics-compatible substrate 314 arranged at a second surface of the power source 302. The power source 302 comprises a hole or cut-out extending therethrough that at least partially defines an isolated communication channel 302a.

The first electronics-compatible substrate 304 comprises one or more sensors 306 disposed thereon, as well as a first transceiver 308. The first electronics-compatible substrate 304 may further comprise a processor 310 and/or memory disposed thereon. The first electronics-compatible substrate 304 is arranged such that the first transceiver 308 is positioned at a first end of the communication channel 302a.

The second electronics-compatible substrate 314 comprises a communication module 316 disposed thereon, as well as a second transceiver 318. The second electronics-compatible substrate 314 is arranged such that the second transceiver 318 is positioned at a second end of the communication channel 302a opposite the first end/the first transceiver 308.

As also previously described, the sensing microsystem 300 may be configured with minimal/no electrical or optical wiring to provide coupling between components. For example, the power source may be electrically coupled to the first and second electronics-compatible substrates 304, 314 via electrical protrusions from the power source 302 as described with reference to FIG. 2. Further, if the communication channel 302a is an optical channel, the optical communication may take place through the air in the channel. Omitting electrical and optical wiring further helps to reduce noise and interference in the microsystem.

Figure 4:
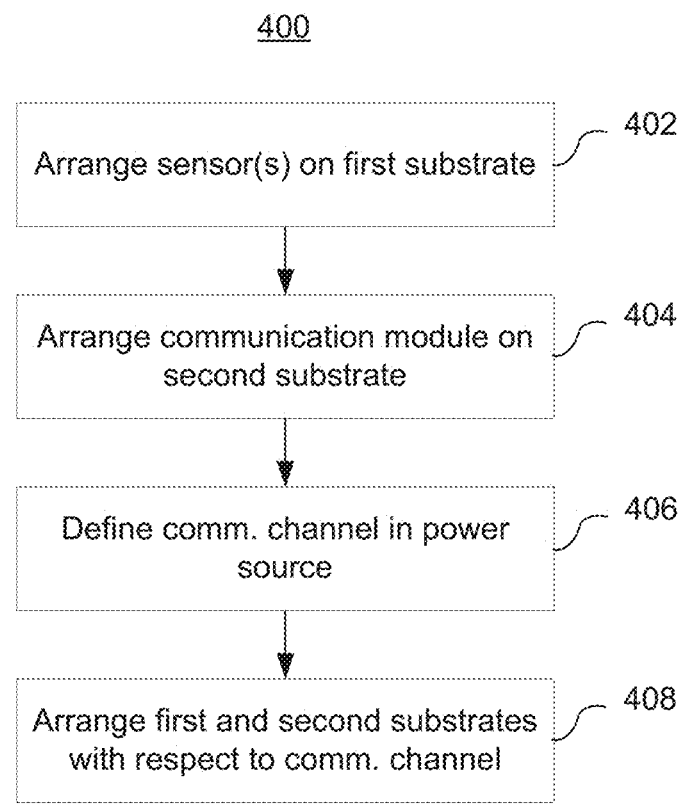
FIG. 4 shows a flow chart of a method of manufacturing the sensing microsystem in accordance with the teachings of the present invention.

FIG. 4 shows a flow chart 400 of a method of manufacturing the sensing microsystem in accordance with the teachings of the present invention.

The method comprises arranging one or more sensors on a first electronics-compatible substrate (402). The sensor(s) may be sensors for measuring one or more physiological parameters of a subject, such as a Photoplethysmography (PPG) sensor, an inertial module comprising accelerometer, gyroscope, and/or magnetometer sensors, a pressure transducer or a pressure switch, a temperature sensor, EEG (Electroencephalography) probes, electrocardiogram (EKG or ECG) probes, bioimpedance and/or biopotential sensors, a sound sensor, a blood-chemical sensor, etc. As previously described, the sensor(s) may be arranged at different locations on the first electronics-compatible substrate to appropriately collect the data of interest. The sensor(s) may also comprise a GPS module for determining a location of the device/subject.

A communication module is arranged on a second electronics-compatible substrate (404). As previously described, the communication module may be configured to communicate with any appropriate short- or long-range wireless communication protocol, including but not limited to Bluetooth™, Zigbee™, Wi-Fi™, Ant+™ 4G, 5G, LTE, or Narrow Band IoT protocols such as LoRa, Sigfox and others, etc.

An isolated communication channel is at least partially defined in a power source (406). For example, as described with reference to FIGS. 2A and 2B one or more holes may be formed in the power source to define the communication channel. Suitable materials such as electrical insulators or opaque optical insulators may be arranged to isolate the communication channel. If the hole is a cut-out that only partially defines the communication channel, the power source may be wrapped with appropriate material to isolate the communication channel.

The first and second substrates are arranged with respect to the communication channel (408). In a particular configuration, the first electronics-compatible substrate is arranged at a first surface of the power source, the second electronics-compatible substrate is arranged at a second surface of the power source opposite the first surface, and the communication channel extends between the first surface and the second surface of the power source. In a further configuration, the one or more sensors are coupled with a first transceiver, the communication module is coupled with a second transceiver, and arranging the first and second electronics-compatible substrates with respect to the channel comprises arranging the first transceiver at a first end of the communication channel and arranging the second transceiver at a second end of the communication channel.

Figure 5:
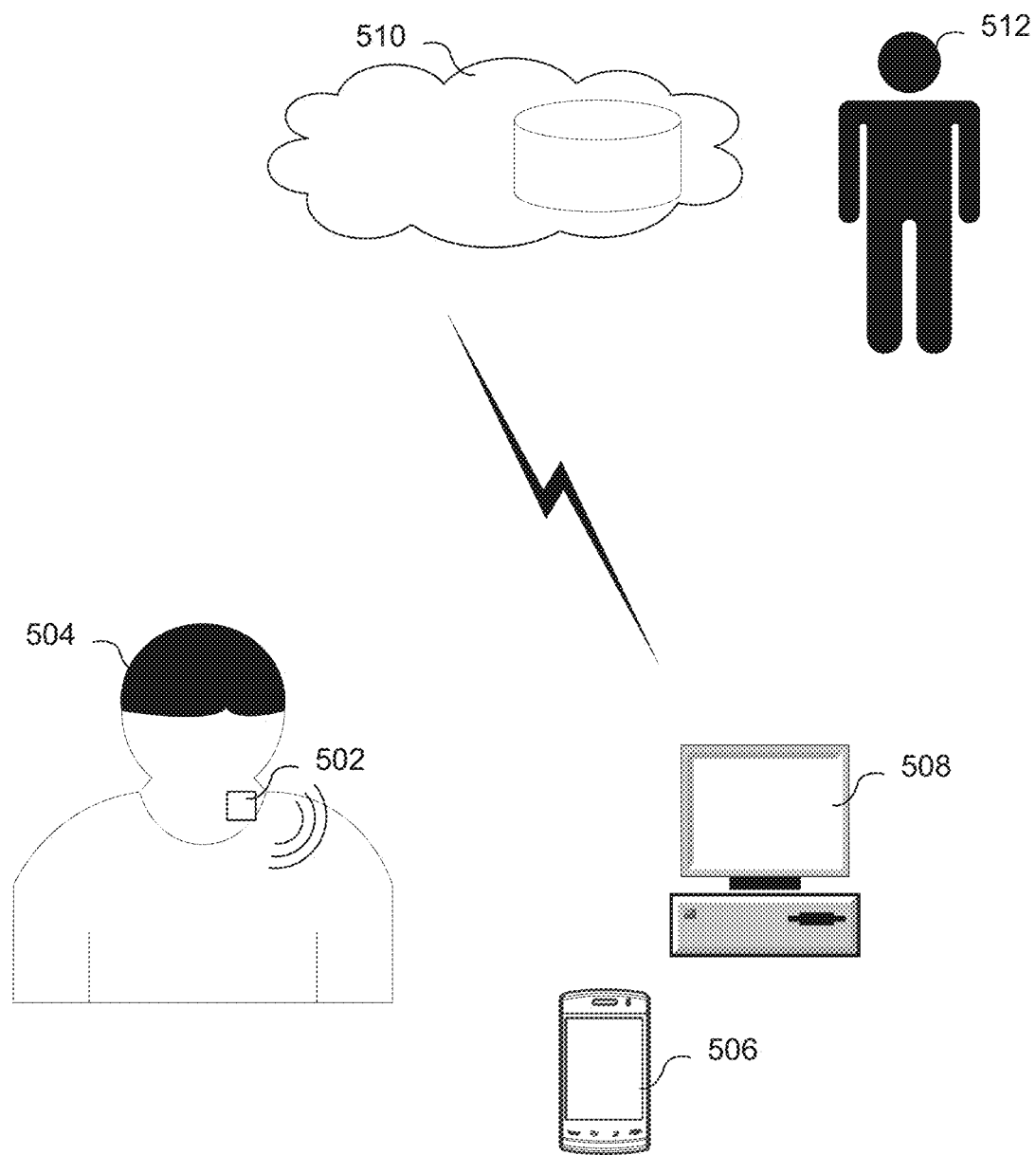
FIG. 5 shows a representation of the sensing microsystem communicating with an external device.

FIG. 5 shows a representation of the sensing microsystem communicating with an external device.

In use, the microsystem may be incorporated into a wearable device to be worn by a subject and/or inserted into a cavity (e.g. oral cavity) of the subject, or may be implanted in the subject. The microsystem (and/or the device it is incorporated into) must be designed for the environmental conditions of the intended application, and may for example be appropriately sealed to prevent moisture/liquid ingress, etc. FIG. 5 shows the microsystem 502 monitoring parameters of subject 504.

As previously described, data collected by the sensors of the microsystem (and possibly processed by a processor) can be sent to an external device via the communication module. For example, the microsystem 502 may transmit data to the subject's personal devices, such as a mobile phone 506 and/or computer 508, where the data can be viewed and/or further processed. Additionally or alternatively, the microsystem 502 may transmit data to remote storage such as in the cloud 510, where it can be accessed by a care provider 512 and/or the subject's devices 506, 508. The data collected by the sensors may relate to one or more vital sign or physiological parameters of the subject. The data collected by the sensors may further comprise location data from a GPS module. In one example use case, monitoring elderly patients with the sensing microsystem disclosed herein would allow for checking vitals if they fell, and which data could then be communicated remotely. Moreover, the GPS could be used for locating the patient, which can similarly be communicated remotely. More generally, however, the sensor data can be used for remote detection/monitoring of various medical conditions, such as sleep disorders, cardio issues like flutter and atrial fibrillation, SIDS, etc. In one embodiment, the Inertial Module Unit (IMU) is also used to detect falls. In a related embodiment, the IMU can be used to detect changes in gait by using AI that examines gait and predicts an increased likelihood of falls.

Various network links may be implicitly or explicitly used in the context of the present invention. While a link may be depicted as a wireless link, it could also be embodied as a wired link using a coaxial cable, an optical fiber, a category 5 cable, and the like. A wired or wireless access point (not shown) may be present on the link between. Likewise, any number of routers (not shown) may be present and part of the link, which may further pass through the Internet.

A method is generally conceived to be a self-consistent sequence of steps leading to a desired result. These steps require physical manipulations of physical quantities. Usually, though not necessarily, these quantities take the form of electrical or magnetic signals capable of being stored, transferred, combined, compared, and otherwise manipulated. It is convenient at times, principally for reasons of common usage, to refer to these signals as bits, values, parameters, items, elements, objects, symbols, characters, terms, numbers, or the like. It should be noted, however, that all of these terms and similar terms are to be associated with the appropriate physical quantities and are merely convenient labels applied to these quantities.

The description of the present invention has been presented for purposes of illustration but is not intended to be exhaustive or limited to the disclosed embodiments. Many modifications and variations will be apparent to those of ordinary skill in the art. The embodiments were chosen to explain the principles of the invention and its practical applications and to enable others of ordinary skill in the art to understand the invention in order to implement various embodiments with various modifications as might be suited to other contemplated uses. The drawings are not necessarily drawn to scale.

What is claimed is:

1. A sensing microsystem, comprising:
   a power source;
   a first electronics-compatible substrate electrically coupled with the power source, the first electronics-compatible substrate having one or more sensors disposed thereon; and
   a second electronics-compatible substrate electrically coupled with the power source, the second electronics-compatible substrate having a communication module disposed thereon,
   wherein the power source defines an isolated optical communication channel extending therethrough between the first electronics-compatible and the second electronics-compatible substrate, the isolated optical communication channel being optically isolated, and wherein the communication module and the one or more sensors are communicatively coupled via the at least one isolated optical communication channel.

2. The sensing microsystem of claim 1, wherein the first electronics-compatible substrate is arranged at a first surface of the power source, the second electronics-compatible substrate is arranged at a second surface of the power source opposite the first surface, and the isolated optical communication channel extends between the first surface and the second surface of the power source.

3. The sensing microsystem of claim 1, wherein the one or more sensors are coupled with a first transceiver disposed at a first end of the isolated optical communication channel, and wherein the communication module is coupled with a second transceiver disposed at a second end of the isolated optical communication channel.

4. The sensing microsystem of claim 1, wherein the communication module is configured to wirelessly communicate with an external device.

5. The sensing microsystem of claim 1, further comprising a processing module communicatively coupled with the one or more sensors and the communication module, and wherein the processing module is configured to receive data from the one or more sensors, perform processing on the data, and send the processed data to the communication module.

6. The sensing microsystem of claim 5, further comprising a memory to store data from the one or more sensors, and/or the processed data.

7. The sensing microsystem of claim 1, wherein the one or more sensors comprise sensors for measuring a physiological parameter of a subject.

8. The sensing microsystem of claim 1, wherein the one or more sensors comprise a GPS module.

9. The sensing microsystem of claim 1, wherein the sensing microsystem has a surface area of length by width of less than 1 cm$^2$.

10. The sensing microsystem of claim 1, wherein the sensing microsystem has a thickness of less than 7 mm.

* * * * *